United States Patent
Ashby et al.

(10) Patent No.: US 9,808,278 B2
(45) Date of Patent: Nov. 7, 2017

(54) TISSUE TRACT LANCET

(75) Inventors: Mark Ashby, Laguna Niguel, CA (US); Eduardo Chi Sing, Dana Point, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 2106 days.

(21) Appl. No.: 11/181,549

(22) Filed: Jul. 14, 2005

(65) Prior Publication Data

US 2006/0116704 A1 Jun. 1, 2006

Related U.S. Application Data

(60) Provisional application No. 60/588,503, filed on Jul. 15, 2004.

(51) Int. Cl.
| | |
|---|---|
| A61B 17/3209 | (2006.01) |
| A61B 17/3211 | (2006.01) |
| A61B 17/34 | (2006.01) |
| A61B 17/32 | (2006.01) |

(52) U.S. Cl.
CPC .... *A61B 17/32093* (2013.01); *A61B 17/3211* (2013.01); *A61B 17/3415* (2013.01); *A61B 2017/320044* (2013.01); *A61B 2017/320052* (2013.01)

(58) Field of Classification Search
CPC ................................................ A61B 17/3209
USPC ........ 606/170, 181, 185, 184; 600/564–567; 128/207.29; 604/164.01, 164.06, 164.13, 604/165.01–165.04, 166.01
See application file for complete search history.

(56) References Cited

U.S. PATENT DOCUMENTS

| | | | |
|---|---|---|---|
| 2,370,319 A | 2/1945 | Lippincott | |
| 2,814,294 A | 11/1957 | Figge | |
| 2,874,776 A | 2/1959 | Hooe | |
| 3,256,874 A * | 6/1966 | De Marco | 600/564 |
| 3,358,689 A | 12/1967 | Higgins | |
| 3,656,479 A * | 4/1972 | Huggins | 604/161 |
| 3,703,174 A | 11/1972 | Smith | |
| 4,000,741 A | 1/1977 | Binard et al. | |
| 4,256,119 A * | 3/1981 | Gauthier | 600/567 |
| 4,405,314 A | 9/1983 | Cope | |
| 4,573,576 A | 3/1986 | Krol | |
| 4,633,860 A * | 1/1987 | Korth et al. | 606/170 |

(Continued)

FOREIGN PATENT DOCUMENTS

| | | |
|---|---|---|
| DE | 36 24 243 A1 | 1/1988 |
| WO | WO96-08208 | 3/1996 |

OTHER PUBLICATIONS

"Sheath Needle for Liver Biopsy in High-Risk Patients," Chuang et al., Radiology 1988; 166:261-262.

(Continued)

*Primary Examiner* — Thomas McEvoy
(74) *Attorney, Agent, or Firm* — Seager, Tufte & Wickhem LLP

(57) ABSTRACT

The present disclosure is a method and apparatus to prepare a tissue tract having a handle member with a centerline, and a scalpel member fixedly attached to the handle member having a blunt tip, wherein the handle member has a first side positioned at a first positive angle relative to the centerline, and a second side opposite the first side positioned at a second positive angle relative to the centerline.

6 Claims, 2 Drawing Sheets

(56) References Cited

U.S. PATENT DOCUMENTS

| | | | |
|---|---|---|---|
| 4,651,752 A * | 3/1987 | Fuerst | 600/567 |
| 4,708,147 A * | 11/1987 | Haaga | 600/566 |
| 4,850,960 A | 7/1989 | Grayzel | |
| 4,929,246 A | 5/1990 | Sinofsky | |
| 4,936,835 A | 6/1990 | Haaga | |
| 4,950,234 A | 8/1990 | Fujioka et al. | |
| 5,053,046 A | 10/1991 | Janese | |
| 5,080,655 A | 1/1992 | Haaga | |
| 5,160,323 A | 11/1992 | Andrew | |
| 5,192,300 A | 3/1993 | Fowler | |
| 5,195,988 A | 3/1993 | Haaga | |
| 5,220,926 A | 6/1993 | Jones | |
| 5,275,616 A | 1/1994 | Fowler | |
| 5,292,309 A | 3/1994 | Van Tassel et al. | |
| 5,326,350 A | 7/1994 | Li | |
| 5,352,233 A | 10/1994 | Anis | |
| 5,437,631 A | 8/1995 | Janzen | |
| 5,447,516 A | 9/1995 | Gardner | |
| 5,467,762 A * | 11/1995 | Sauer et al. | 600/114 |
| 5,476,480 A * | 12/1995 | Matsutani et al. | 606/222 |
| 5,478,352 A | 12/1995 | Fowler | |
| 5,507,279 A | 4/1996 | Fortune et al. | |
| 5,527,332 A | 6/1996 | Clement | |
| 5,545,175 A | 8/1996 | Abidin et al. | |
| 5,690,664 A * | 11/1997 | Sauer et al. | 606/185 |
| 5,807,276 A * | 9/1998 | Russin | 600/567 |
| 5,820,628 A * | 10/1998 | Middleman et al. | 606/147 |
| 5,827,305 A * | 10/1998 | Gordon | 606/159 |
| 5,843,108 A * | 12/1998 | Samuels | 606/167 |
| 6,264,668 B1 * | 7/2001 | Prywes | 606/167 |
| 6,413,265 B1 | 7/2002 | Goodwin | |
| 6,416,484 B1 * | 7/2002 | Miller et al. | 600/564 |
| 6,544,277 B1 * | 4/2003 | O'Heeron et al. | 606/185 |
| 6,551,253 B2 * | 4/2003 | Worm et al. | 600/564 |
| 6,685,717 B1 | 2/2004 | Llic | |
| 6,716,228 B2 * | 4/2004 | Tal | 606/167 |
| 6,827,692 B2 * | 12/2004 | Castellacci | 600/567 |
| 6,830,578 B2 * | 12/2004 | O'Heeron et al. | 606/185 |
| 2002/0040231 A1 * | 4/2002 | Wysoki | 606/185 |
| 2004/0181246 A1 * | 9/2004 | Heppler | 606/167 |

OTHER PUBLICATIONS

Partial International Search Report PCT/US2005/024844; report dated Nov. 23, 2005.

* cited by examiner

TISSUE TRACT LANCET

CROSS REFERENCE TO RELATED APPLICATION

This non-provisional application claims the priority benefit under 35 USC 119(e) of U.S. Provisional Application No. 60/588,503, filed Jul. 15, 2004.

FIELD OF THE DISCLOSURE

The present disclosure generally relates to medical devices, and more particularly, the present disclosure relates to surgical scalpels, including surgical scalpels for the preparation of a tissue tract.

BACKGROUND OF THE DISCLOSURE

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Tissue tract preparation prior to advancement of extravascular devices, such as depth markers or delivery tools, is important to the outcome of the closure procedure. For example, there may be times where a 12 Fr tool must be advanced into a tissue tract created by a 4 Fr to 8 Fr access sheath. As a result, the tissue tract must be prepared to receive the 12 Fr tool. Currently, tissue tracts are prepared using common surgical scalpels that do not allow a surgeon to create consistent tissue tract incisions and do not allow a surgeon to make accurately sized incisions.

Thus, there is a need for a device that will allow a user to create the same tissue tract incisions. Moreover, there is a need for a device which will allow a user to create accurate tissue tract incisions.

SUMMARY OF THE DISCLOSURE

In accordance with one aspect of the disclosure, an apparatus to prepare tissue tract is disclosed which comprises a handle and a scalpel blade. The handle lies in a first plane while the scalpel blade extends from the handle and is non-coplanar with the first plane of the handle.

In accordance with another aspect of the disclosure, an apparatus for preparing a tissue tract is disclosed which comprises a guide member, and a tissue tract lancet mounted over the guide member. The tissue tract lancet includes a handle and a scalpel blade extending from the handle.

These and other aspects and features of the disclosure will become more apparent upon reading the following detailed description when taken in conjunction with the accompanying drawings.

Figure 1:
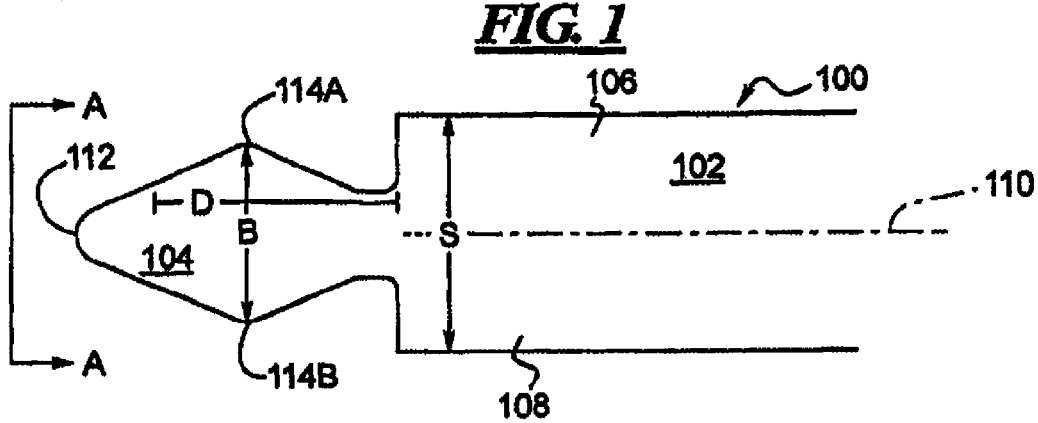
FIG. 1 is a plan view of an apparatus constructed in accordance with an embodiment of the present disclosure.

While the disclosure is susceptible to various modifications and alternative constructions, certain illustrative embodiments thereof have been shown in the drawings that will be described in detail below. It should be understood, however, that there is no intention to limit the disclosure to the specific form disclosed, but on the contrary, the intention is to cover all modifications, alternative constructions, and equivalents falling within the spirit and scope of the disclosure as defined by the appended claims.

DETAILED DESCRIPTION FOR DISCLOSURE

Embodiments of the present disclosure are described herein in the context of a tissue tract lancet. Those of ordinary skill in the art will realize that the following detailed description of the present disclosure is illustrative only and is not intended to be in any way limiting. Other embodiments of the present disclosure will readily suggest themselves to such skilled persons having the benefit of this disclosure. Reference will now be made in detail to implementations of the present disclosure as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1A:
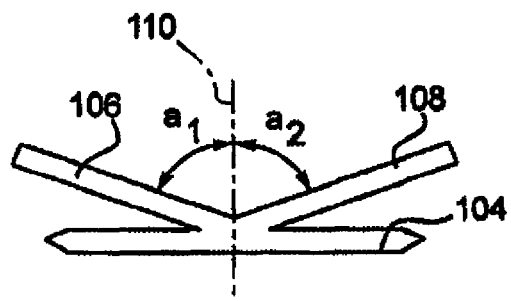
FIG. 1a is a front view of FIG. 1 taken along line A-A of FIG. 1.

The present disclosure provides for a device that will allow a user to create accurate tissue tract incisions. Referring now to FIGS. 1 and 1a, an illustration in accordance with an embodiment of the present invention. The device, generally numbered 100, has a handle member 102 and a scalpel member 104 attached to the handle member 102. The handle member 102 may have a first side 106 and a second side 108, the first side 106 positioned opposite the second side 108 along the centerline 110 of the handle member 102. As illustrated in FIG. 1a, a front view of FIG. 1 along axis A-A, first side 106 is positioned at a negative angle $a_1$ and second side 108 is positioned at an equal but positive angle $a_2$ relative to centerline 110 thereby creating a second and third plane in the shape of a "V". Accordingly, it can be seen that the handle 102 is not in the same plane as the scalpel 104, or in other words is non-coplanar with the scalpel. Positioning the first side 106 and second side 108 at an angle relative to centerline 110 allows a user to engage the device at the skin surface of a patient and acts as a stop. Scalpel member 104 may have a blunt tip 112 to prevent injury to the blood vessel when the device 100 is inserted into the tissue tract and to help tension or taut the tissue prior to encountering the cutting surface. Apex 114a, 114b may be blunt as shown in FIG. 1. This helps to post-tension the tissue after encountering the cutting portion of the tissue tract. However, apex 206a, 206b may also be sharp as illustrated in FIG. 2.

By way of example only and not intended to be limiting, if a user would like to create a tissue tract for a 12 Fr device, such as a depth marker or delivery system, then dimensions of the device 100 maybe used to and in such preparation. For example, paramodes B, S and D can be used wherein 3 mm≤B≥5 mm; 3 mm≤S≥10 mm; and 7 mm≤D≤13 mm as shown in FIG. 1. Other dimensions are certainly possible.

The present disclosure may be manufactured from SST sheet, as the profile can readily be punched. The "V" cross section may be formed by a manufacturing process such as a punch press. Areas that are desired to be sharpened, such as apex 206a, 206b may be sharpended by any process such as grinding.

Figure 2:
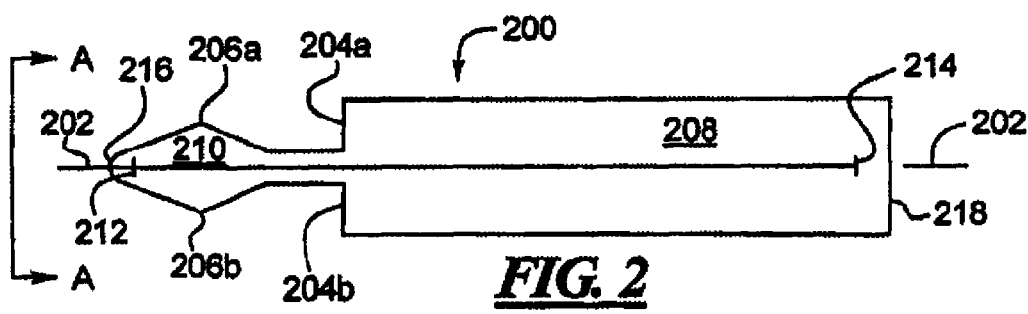
FIG. 2 is a plan view of an apparatus constructed in accordance with another embodiment of the present disclosure.
Figure 2A:
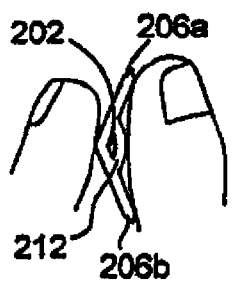
FIG. 2a is a front view of FIG. 2 taken along line A-A of FIG. 2.

FIGS. 2 and 2a illustrate another embodiment of the present disclosure used over a guidewire. The device 200 has a handle member 208 and a scalpel member 210. The handle member 208 and scalpel member 210 may both be angled relative to the centerline (not shown) of device 200 as illustrated in FIG. 2a, a front view of FIG. 2 along axis A-A.

The device 200 may be advanced over a guidewire 202 already in the tissue tract. The guidewire 202 runs along the centerline of device 200 and is inserted through guide tabs 212, 214 located near blunt tip 216 and handle end 218, respectively. Handle member 208 and scalpel member 210 are both "V" shape to allow the user to grip the handle without gripping the guidewire 202. The guidewire 202 assures that the device precisely modifies the tissue tract only since it acts as a monorail centrally located within the tissue tract.

The "V" shape allows apex 206a, 206b to have forward and/or rear forward facing cutting surfaces. It also allows scalpel member 210 to have a sharpened edge on the top and/or bottom surface of scalpel member 210. In so doing, forward and rearward facing cutting surfaces laterally flank each apex 206a and 206b.

Figure 2B:
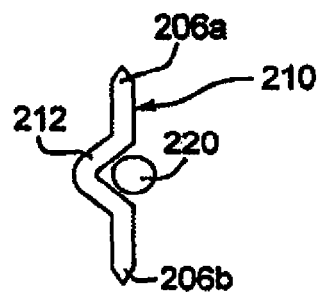
FIG. 2b is a front view of another alternative embodiment.

Those of ordinary skill in the art will now realize that the present disclosure may be used over other surgical devices such as a needle, access sheath 220 (shown in FIG. 2b), guide catheter, or similar devices. The present disclosure may be positioned over the other surgical devices similar to how the guidewire is positioned as described and shown in FIGS. 2 and 2a. As illustrated in FIG. 2b, the scalpel member 210 need not be in a "V" shape.

Figure 3A:
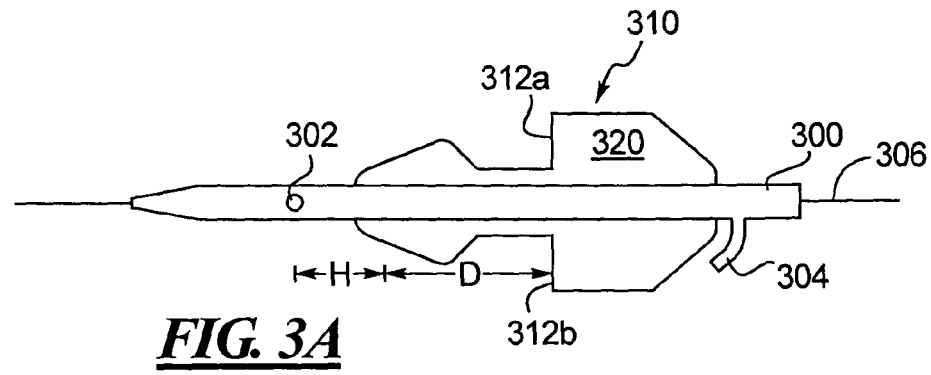
FIG. 3a is a plan view of another embodiment of an apparatus constructed in accordance with the teachings of the disclosure.
Figure 3B:
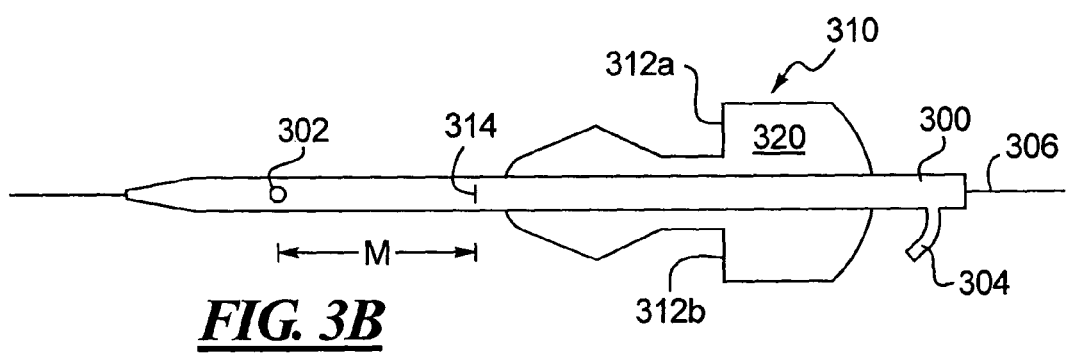
FIG. 3b is a plan view of another alternative embodiment using a dilator.
Figure 3C:
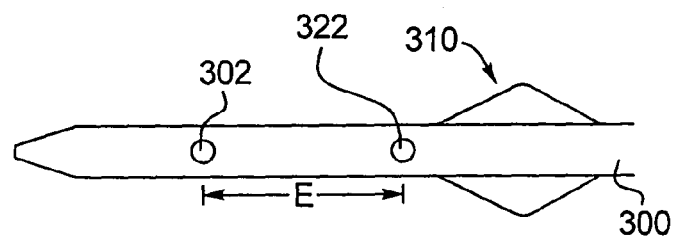
FIG. 3c is a plan view of another alternative embodiment using a dilator.

FIGS. 3A, 3B, and 3C illustrate the present invention in use with a dilator. The dilator 300 may be positioned over a guidewire 306 and may have a bleed back entrance port 302 and a bleed back exit port 304. In use, when placed in a tissue tract and within a blood vessel, blood will enter the bleed back entrance port 302 and exit the bleed back exit port 304. this informs the user of the location of the blood vessel puncture site. A depth marker 308 may also be used with the dilator. The depth marker may be an O-ring or may be markers on the dilator 300 shaft. A more detailed explanation of the dilator and depth marker may be found in 1. U.S. patent application Ser. No. 09/859,682, entitled "Depth and Puncture Control for Blood Vessel Hemostasis System", filed May 18, 2001 by inventors Mark Ashby, Andrew Cragg, Luis Urquidi, Eduardo Chi Sing, and Eric Lee; 2. U.S. patent application Ser. No. 10/007,204, entitled "System and Method for Delivering Hemostasis Promoting Material to a Blood Vessel Puncture Site by Fluid Pressure", filed Nov. 8, 2001 by inventor Mark Ashby; and 3. U.S. patent application Ser. No. 10/421,680, entitled "Puncture Closure System with Pin and Pull Technique", filed Apr. 22, 2002 by inventors Thomas David, Mark Ashby, and Eduardo Chi Sing which are all incorporated herein by reference in their entirety.

The device 310 may be positioned a distance H from the bleed back entrance port 302, which may also be the minimum distance from the vessel puncture site. Distance D may be the maximum depth of the vessel puncture site from the patience's skin. The dilator 300 and device 310 are simultaneously advanced until bleed back is observed out of the bleed back exit port 304 or until shoulders 312a, 312b encounter the patient's skin. If bleed back is not observed out of bleed back exit port 304 and shoulders 312a, 312b encountered the patient's skin, the user should discontinue the procedure.

FIG. 3B illustrates the embodiment similar to FIG. 3A, having an indicator line 314 located a distance M from the bleed back entrance port 302. Distance M is the minimum tract depth desired for a successful closure of the blood vessel puncture. The dilator 300 and device 310 are simultaneously advanced through the tissue tract until the indicator line 314 reaches the patient's skin surface. If bleed back out of the bleed back exit port 304 is observed, the user should discontinue the procedure. If no bleed back is observed, the dilator 300 is advanced until shoulders 312a, 312b reaches the patient's skin.

FIG. 3C is similar to FIG. 3B, except a bleed back indicator hole 322 is used instead of the indicator line 314. The bleed back indicator hole 322 is positioned a distance E from the bleed back entrance port 302, where distance E is the minimum tract depth desired for successful closure. The dilator 300 and device 310 are simultaneously advanced through the tissue tract until the bleed back indicator hole 322 is above the patient's skin surface. If bleed back is observed out of the bleed back indicator hole 322, closure of the blood vessel puncture is discontinued. However, if bleed back is not observed, the closure process continues and the device 310 and dilator 300 are advanced until shoulders (not shown) connect with the patient's skin.

Figure 3D:
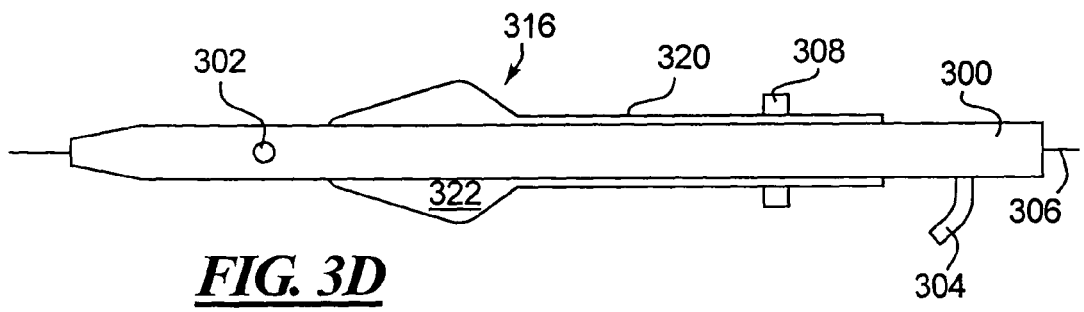
FIG. 3d is a plan view of another alternative embodiment using a dilator.

FIG. 3D illustrates another embodiment similar to FIGS. 3A and 3B, having a depth marker 308. The device 316 has a scalpel member 322 and handle member 320. The dilator 300 is advanced into the tissue tract until bleed back out of the bleed back exit port 304 is observed. To mark the depth of the blood vessel puncture site, the depth marker 308 around handle member 320 may be positioned at the patient's skin surface. Alternatively, the user may mark the dilator shaft or measurements may already be positioned on the dilator 300 or handle member 322 itself. The device 316 may then be withdrawn from the dilator 300 and used to compare it with other extravascular devices, such as delivery systems, to inform the user of the depth of blood vessel puncture site. This allows the user to consistently prepare the tissue tract to the same distance from the blood vessel.

While embodiments and applications of this disclosure have been shown and described, it would be apparent to those skilled in the art having the benefit of this disclosure that many more modifications then mentioned above are possible without departing from the inventive concepts herein. The invention, therefore, is not to be restricted except in the spirit of the appended claims.

What is claimed is:

1. An apparatus to prepare a tissue tract, comprising:
   a proximal handle portion comprising a generally planar first section positioned opposite to a generally planar second section along a center line;
   a distal scalpel blade portion extending from the handle and fixedly attached thereto, the scalpel blade being non-coplanar with the first and second sections of the handle, the scalpel blade being divided by the center line into first and second sides, the first and second sides joined by a blunt tip; and
   wherein the scalpel blade further includes a first side apex disposed on the first side and a second side apex disposed on the second side opposite to the first side apex relative to the center line, and the first and second side apices are sharp and located distal of the handle.

2. The apparatus of claim 1, wherein the scalpel blade includes forward and rearward facing cutting surfaces laterally flanking each apex.

3. An apparatus for preparing a tissue tract, comprising:
   a guide member;
   a tissue tract lancet mounted over the guide member, the tissue tract lancet including a proximal handle portion and distal scalpel blade portion extending from the handle and fixedly attached thereto; and
   wherein the scalpel blade further includes a blunt tip, a first side apex and a second side apex opposite to the first side apex relative to a center line disposed along the handle, and the first and second side apices are sharp.

4. The apparatus of claim 3, wherein forward and rearward facing cutting surfaces laterally flank the first and second side apices.

5. An apparatus for preparing a tissue tract, comprising:
   a guide member;
   a tissue tract lancet including:
      a proximal handle portion disposed along a center line including a first generally planar section positioned opposite a second generally planar section along the center line;
      a distal scalpel blade portion fixedly attached to and extending from the handle along the center line including a first side, a second side, a first side apex disposed on the first side, and a second side apex disposed on the second side; and
      at least one guide tab;
   wherein the guide member is inserted into the at least one guide tab;
   wherein the first side of the scalpel blade is positioned opposite the second side of the scalpel blade relative to the center line;
   wherein the first side apex is positioned opposite to the second side apex relative to the center line;
   wherein the first and second sides of the scalpel blade further include forward and rearward facing cutting surfaces laterally flanking each apex, and the first and second sides of the scalpel blade are non-coplanar with the first and second generally planar sections of the handle;
   wherein the forward facing cutting surfaces are joined by a blunt tip.

6. The apparatus of claim 5, wherein the first and second sides of the scalpel blade are coplanar.

* * * * *